United States Patent [19]

Brown et al.

[11] Patent Number: 4,637,986
[45] Date of Patent: Jan. 20, 1987

[54] FLOW CYTOMETRY LYSING REAGENT WITH LEUKOPROTECTIVE AGENT FOR PRODUCING A 3-PART WBC COUNT

[75] Inventors: Michael C. Brown, Wayland; Stefan J. Kirchanski, Framingham, both of Mass.

[73] Assignee: Ortho Diagnostic Systems, Inc., Raritan, N.J.

[21] Appl. No.: 525,575

[22] Filed: Aug. 22, 1983

[51] Int. Cl.$^4$ .................................................. G01N 31/00
[52] U.S. Cl. ........................................ 436/10; 436/17; 436/18
[58] Field of Search ................................ 436/8–18; 252/408.1; 424/2, 3, 4; 435/2

[56] References Cited

U.S. PATENT DOCUMENTS

| | | | |
|---|---|---|---|
| 3,874,852 | 4/1975 | Hamill | 23/230 B |
| 3,956,477 | 5/1976 | Price et al. | 424/8 |
| 4,011,045 | 3/1977 | Bonderman | 436/13 |
| 4,040,785 | 8/1977 | Kim et al. | 436/17 |
| 4,099,917 | 7/1978 | Kim | 23/230 B |
| 4,185,964 | 1/1980 | Lancaster | 23/230 B |
| 4,198,206 | 4/1980 | Ryan | 436/17 |
| 4,199,471 | 4/1980 | Louderback et al. | 436/17 |
| 4,244,837 | 1/1981 | Crews et al. | 436/17 |
| 4,286,963 | 9/1981 | Ledis et al. | 23/230 B |
| 4,465,774 | 8/1984 | Huang et al. | 436/17 |
| 4,493,821 | 1/1985 | Harrison | 436/17 |
| 4,517,301 | 5/1985 | Greene | 436/14 |

OTHER PUBLICATIONS

Sha'afi, R. I. et al., "Permeability of Red Cell Membranes to Small Hydrophilic and Lipophilic Solutes", Journal of General Physiology, 58:238–258 (1971).
Jacobs, M. H. et al., "Osmotic Properties of the Erythrocyte", J. Cellular Comp. Physiol., 7, 197–225 (1935).
Hammarlund, E. R. et al., "Hemolysis of Erythrocytes in Various Iso-osmotic Solutions", J. Pharmaceutical Sciences, 50, 1:24–30 (1961).
Hober, R., "The Permeability of Red Blood Corpuscles to Organic Anions", J. Cellular Comp. Physiol., 7, 367–389 (1935).
Sapp, C. et al., "Sodium Chloride Equivalents, Cryoscopic Properties, and Hemolytic Effects of Certain Medicinals in Aqueous Solution III", Journal of Pharmaceutical Sciences, 64, 11:1884–1886 (1975).
Hammarlund, E. R. et al., "Sodium Chloride Equivalents, Cryoscopic Properties, and Hemolytic Effects of Certain Medicinals in Aqueous Solution", J. Pharmaceutical Sciences, 55, 12:1448–1451 (1966).
Fassett, W. E. et al., "Sodium Chloride Equivalents, Cryoscopic Properties, and Hemolytic Effects of Certain Medicinals in Aqueous Solution II", J. Pharmaceutical Sciences, 58, 12:1540–1542 (1969).

*Primary Examiner*—John F. Terapane
*Assistant Examiner*—T. J. Wallen
*Attorney, Agent, or Firm*—Audley A. Ciamporcero, Jr.; Mark A. Hofer

[57] ABSTRACT

Lysing reagents for use in flow cytometry instruments. Lysing reagents suitable for lysing red blood cells are provided thereby permitting 3-part differential counting of white blood cells. The reagents comprise a leukoprotective agent for preserving the lymphocyte cellular integrity during analysis, and buffers adjusted to provide the correct pH environment for optimal lysis and activity. Preferred embodiments will additionally incorporate non-ionic preservatives in very low concentrations.

4 Claims, No Drawings

FLOW CYTOMETRY LYSING REAGENT WITH LEUKOPROTECTIVE AGENT FOR PRODUCING A 3-PART WBC COUNT

FIELD OF THE INVENTION

This invention relates to lysing reagents and specifically relates to lysing reagents containing leukoprotective agents useful for producing a standard 3-part differential white blood cell count in a flow cytometry type of instrument.

BACKGROUND OF THE INVENTION

The need to supply the clinical environment with automated instrumentation has forced the development of a wide variety of instruments capable of performing various types of blood cell counts. Automated counting of red blood cells or erythrocytes, platelets, or leukocytes white blood cells may be accomplished by a variety of techniques. One class of instruments includes, for instance, those based on flow cytometry principles and may generally be described as operating by analyzing light scatter characteristics of cells which are individually passed in a single stream analysis through an area illuminated by a focused light source. Typically lasers are employed to provide the illumination required and the scatter measurements are taken in a plurality of angles.

Often, it becomes necessary to remove the scatter effects produced by one class of cells in order to preserve the accuracy of counts with respect to another class. This may be accomplished by employing a lysing reagent specific for the class of interest.

Presently, the assignee hereof commercially offers the ELT series of instruments which are capable of providing red blood cell, white blood cell and platelet counts as well as the five traditional parameters: HGB, HCT, MCV, MCH and MCHC. Recently however, the assignee has experienced an increasing demand by clinicians for white blood cell differential counts, i.e., the so-called 3-Part Dif counts. This requires additional instrument capability so that the three leukocyte subpopulations (lymphocytes, granulocytes and monocytes) can be enumerated. In order to accomplish this, it becomes necessary to selectively lyse the red blood cells without significantly and deleteriously affecting the scatter characteristics of white blood cells.

It is an object of the present invention to provide reagents which are capable of lysing the red blood cells without disadvantageously affecting the white blood cells while their light scatter measurements are being detected.

It is a further object that the lysing reagent operate with sufficient speed so that the throughput of the interrogating instruments are not deleteriously effected thereby.

It is another object of the present invention to provide a red blood cell lysing reagent having a leukoprotective action for use in an upgraded ELT series instrument whereby 3-Part Dif counts may be obtained.

SUMMARY OF THE INVENTION

In accordance with the principles and objects of the present invention there are provided lysing reagents comprising a hydrophilic penetrating molecule selected from the list provided in Table 1; an organic, nitrogen containing buffer such as TRIS or 2-amino-2-methyl-1,3-propanediol and an ethane sulfonic acid buffer such as HEPES or TAPS so that the total buffer concentration is below 10 mM. Preferably, the buffers will be adjusted to have a pH within the range of approximately pH 8.1 to 8.8. Preferred embodiments will additionally comprise preservatives such as phenoxyethenol and/or neomycin sulfate.

DETAILED DESCRIPTION OF THE INVENTION AND BEST MODE

Selection of the pH at which the lysing reagent operates is important from two aspects, if the pH is relatively low, then lysis occurs at a greatly reduced rate resulting in a disadvantageous delay. Such a delay will adversely affect throughput. On the other hand, excessively high pH values, for instance those in excess of pH 9.0, have been discovered to cause rapid deterioration of the leukocytes. Leukocyte deterioration disadvantageously affects counting accuracy. It has been discovered by the inventors hereof that the preferred pH range from approximately 8.1 to 8.8 with an optimal pH occurring in the neighborhood of pH 8.5.

It has been further discovered that the specific buffering agent employed is critical to the proper operation of the lysing reagent. Ideally, the buffer shall exhibit a pka close to the optimum or desired pH. Since the presence of the buffer itself will tend to act as a solute and therefore osmotically slow the lytic process, the ideal buffer will be selected to provide a high buffering capacity thereby necessitating a low concentration thereof, thus limiting its osmotic effects. Indeed, in combination with the hydrophilic penetrating molecule of the present invention, selected from Table 1, the inventors hereof have found it essential to keep the total buffer concentration below 10 mM.

It has still further been discovered that due to the effects of the buffering agent upon the ion channels in the erythrocyte membrane, mineral buffers such as phosphate and carboxylic acids or molecules containing a carboxyl group are not effective. Rather, the preferred buffering agents are organic, nitrogen containing buffers such as TRIS or 2-amino-2-methyl-1,3-propanediol. In combination with these organic bases, the most favorable acidic components to use are the ethane sulfonic acid "Good Buffers" such as HEPES or TAPS. In the alternative, boric acid may be used by itself or more advantageously with TRIS (another "Good Buffer"), however, the inventors hereof have found it to be less effective than the aforementioned buffer combinations. The most preferred buffer is the combination of 5 mM TRIS with 2.5 mM TAPS.

The "Good Buffers" which are suitable, are fully described in Good et al, Biochemistry, 5,467-77 (1966). HEPES is N-2-hydroxyethyl piperazine-N'-2-ethane sulfonic acid. TAPS is N-tris-(hydroxymethyl)methyl-3-aminopropane sulfonic acid, and TRIS is tris-(hydroxymethyl)aminomethane.

Although water is a buffered state will, by itself, rapidly lyse red cells in a majority of biological samples, there will be a significant loss of leukocytes associated therewith, particularly within the lymphocyte subclass. Such a loss is, of course, preferably avoided as it will deleteriously affect the counting. Accordingly, it becomes necessary to add a solute which will slow the rate of lysis of the leukocytes. In the embodiments of the present invention, these solutes will additionally act to protect the leukocytes from lysis. Although the addition of virtually any solute will osmotically slow lysis, the inventors hereof have found that only those solutes which are small, hydophilic and lipid bilayer penetrators, provide the leukoprotective action desired. These compounds protect the leukocytes, and in particular the lymphocytes, by a mode of action which is, however, difficult to determine. It is, however, clear that proper selection of the leukoprotective agent results in significantly higher and more stable lymphocyte counts on upgraded ELT instruments still under development. It is not clear however, whether the protective mechanism involves a stabilizing alteration of the leukocyte membranes or whether it is related to a stabilizing buildup of the solute agent within the leukocyte cytoplasm.

As an additional advantage, it has been discovered that the preferred leukoprotective agents, by their presence, produce superior resolution between cellular debris and leukocytes. Again, the mechanism underlying this effect is somewhat unclear, but may result from a direct effect on the erythrocyte lysis or from an optical effect on the debris following lysis.

The inventors hereof, however, believe, without wishing to be held to such belief, that the effectiveness of the leukoprotective agent, within each group of preferred leukoprotective agents as set forth in Table 1, is related to the chain length of the molecule. For instance, butoxyethanol, the most preferred leukoprotective agent, has been found more effective than ethoxyethanol which is more effective than methoxyethanol. This relationship between the longer, more lipid soluble molecules and their effectiveness tends to suggest that alteration of the membrane fragments occurs by intercalation of the lipid-soluble agent is the responsible mechanism for the observed effect of decreasing debris.

In all cases, however, the operation of the leukoprotective, debris altering agents is strongly concentration dependent. At very low concentrations, some lymphocytes undergo lysis and the debris may become significant. At optimum concentrations, the lymphocytes are protected and the debris minimized while at greatly increased concentrations, the leukocyte light scatter is disadvantageously altered and the erythrocytes fail to lyse. The failure of red blood cells to lyse may be related to the change in osmolarity of the solution or to stabilization of the erythrocyte membrane by the agent in a manner similar to that occurring in the leukocytes. Accordingly, the inventors have discovered the most preferred embodiment will employ the leukoprotective agent, butoxyethanol, in a concentration of about 60 mM.

The most preferred embodiments will additionally comprise a preservative in order to avoid the growth of bacteria and fungi. Because many pharmaceutical preservatives cause excessive lysis or osmotically prevent lysis, they are not suitable for use. Instead, the ideal preservative will be non-ionic and effective in extremely low concentrations thereby minimizing its osmotic effects. Although the instant lysing reagent does not require a preservative for action, a preferred embodiment will incorporate 4 mM phenoxyethanol and 1.0 mg/l neomycin sulfate as preservatives thereby increasing shelf life.

Table 1 presents the preferred leukoprotective agents of the present invention, with the most preferred agents provided in Group B. The best mode contemplated by the inventors will employ butoxyethanol as the lymphoprotective agent.

TABLE 1

| LEUKOPROTECTIVE AGENT | APPROXIMATE OPTIMAL CONC. | PREFERRED RANGE |
| --- | --- | --- |
| Group A | | |
| Methanol | 500 mM | 300–700 mM |
| Ethanol | 400 | 200–600 |
| Propanol | 150 | 50–500 |
| Butanol | 70 | 20–500 |
| Pentanol | 35 | 10–250 |
| Group B | | |
| Methoxyethanol | 250 mM | 100–700 mM |
| Ethoxyethanol | 120 | 50–500 |
| Butoxyethanol | 60 | 10–300 |
| Methoxyethoxyethanol | 150 | 50–400 |
| Ethoxyethoxyethanol | 100 | 10–300 |
| Butoxyethoxyethanol | 50 | 10–300 |
| Group C | | |
| Ethylene glycol | 325 mM | 150–600 mM |
| Propylene glycol | 250 | 150–500 |
| Group D | | |
| Ethyl ether | 250 mM | 100–500 mM |
| Ethylene glycol dimethyl ether | 100 | 25–400 |
| Ethylene glycol diethyl ether | 75 | 25–250 |
| 2-Methoxyethyl ether | 75 | 25–250 |
| Tetrahydrofuran | 275 | 100–500 |
| Group E | | |
| Acetone | 250 mM | 50–500 mM |
| Methyl ethyl ketone | 275 | 50–500 |
| Acetonitrile | 400 | 50–600 |
| Nitromethone | 300 | 50–500 |
| Ethyl acetate | 120 | 25–300 |
| 2-Methoxyethyl acetate | 80 | 20–250 |
| Group F | | |
| Dioxane | 450 mM | 200–600 mM |
| Pyridine | 350 | 300–700 |
| Imidazole | 225 | 100–400 |
| N—methylpyrrolidone | 250 | 150–450 |
| Dimethylacetamide | 450 | 200–600 |
| Dimethylformamide | 400 | 200–600 |
| Formamide | 450 | 200–600 |
| Dimethylsulfoxide | 200 | 50–400 |
| 1-Dodecyl-aza-cyclo-heptane-2-one | 150 | 50–400 |

It will be readily appreciated by those skilled in the art that various alterations of the foregoing may be made without departing from the spirit or scope of the present invention.

We claim:

1. A lysing reagent for use in a flow cytometry instrument comprising: a combination of an organic, nitrogen containing buffer selected from the group consisting of TRIS and 2-amino-2-methyl-1,3-propanediol, and an ethane sulfonic acid buffer selected from the group consisting of HEPES and TAPS; and a leucoprotective agent selected from the group consisting of methyoxyethanol at a concentration of 100–700 mM, ethoxyethanol or methoxyethoxyethanol at a concentration of 50–500 mM, butoxyethanol or ethoxyethoxyethanol or butoxyethoxyethanol at a concentration of 10–300 mM.

2. The reagent as provided in claim 1 wherein the leukoprotective agent is butoxyethanol.

3. The reagent as provided in claim 1 wherein the leukoprotective agent selected from Group B is present at approximately the optimal concentration listed in Table 1.

4. A lysing reagent comprising butoxyethanol present in the range of about 60 mM, TRIS buffer present in the range of about 5 mM and TAPS buffer present in the range of about 2.5 mM.

* * * * *